United States Patent [19]

Ito et al.

[11] Patent Number: 5,744,653
[45] Date of Patent: Apr. 28, 1998

[54] METHOD FOR PREPARING 1,3-DIHYDROXY-4,6-BIS(α-METHYL-α(4'-HYDROXYPHENYL)ETHYL)BENZENE

[75] Inventors: Mizuo Ito; Shigeru Iimuro, both of Aichi, Japan

[73] Assignee: Mitsui Toatsu Chemicals, Inc., Tokyo, Japan

[21] Appl. No.: 699,190

[22] Filed: Aug. 19, 1996

Related U.S. Application Data

[63] Continuation of Ser. No. 390,791, Feb. 17, 1995, abandoned.

[30] Foreign Application Priority Data

Feb. 25, 1994 [JP] Japan ................................. 6-027729
Sep. 13, 1994 [JP] Japan ................................. 6-218751

[51] Int. Cl.⁶ ..................................................... C07C 39/12
[52] U.S. Cl. .................................................. 568/720; 568/718
[58] Field of Search ................................... 568/718, 720

[56] References Cited

FOREIGN PATENT DOCUMENTS 4-364147  12/1992  Japan ........................ 568/720
6116191   4/1994   Japan ........................ 568/720

*Primary Examiner*—Alan Siegel
*Attorney, Agent, or Firm*—Burns, Doane, Swecker & Mathis

[57] ABSTRACT

A method for preparing 1,3-dihydroxy-4,6-bis[α-methyl-α-α(4'-hydroxyphenyl)ethyl]benzene represented by the following formula (1):

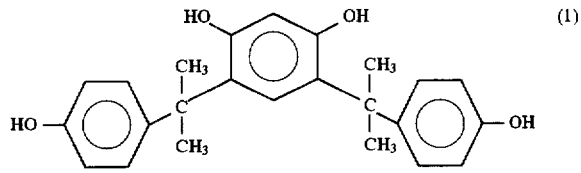

comprising the step of initiating a reaction of resorcin with 4-isopropenylphenol in a mixed solvent which comprises a non-polar solvent and a polar solvent in the presence of an acidic catalyst. The method can easily be handled, ensures a high yield, permits the reduction of impurity content and can provide highly pure 1,3-dihydroxy-4,6-bis[α-methyl-α-(4'-hydroxyphenyl)ethyl]benzene. The resulting phenolic compound is useful as, for instance, a branching agent for polycarbonates, polyesters or the like; a raw material for radiant ray-sensitive components for use as resist materials; a raw material for epoxy resins; and a hardening agent for epoxy resins.

8 Claims, No Drawings

METHOD FOR PREPARING 1,3-DIHYDROXY-4,6-BIS(α-METHYL-α(4'-HYDROXYPHENYL)ETHYL)BENZENE

This application is a continuation of application Ser. No. 08/390,791, filed Feb. 17, 1995 now abandoned.

BACKGROUND OF THE INVENTION

(a) Field of the Invention

The present invention relates to a method for preparing 1,3-dihydroxy-4,6-bis[α-methyl-α-(4'-hydroxyphenyl) ethyl]benzene.

More specifically, the present invention relates to a method for preparing 1,3-dihydroxy-4,6-bis[α-methyl-α-(4'-hydroxyphenyl)ethyl]benzene which is useful as, for instance, a branching agent for polycarbonates, polyesters or the like; a raw material for radiant ray-sensitive components for use as resist materials; a raw material for epoxy resins; and a hardening agent for epoxy resins.

(b) Description of the Prior Art

Japanese Un-examined Patent Publication No. Hei 4-364147 discloses a method for preparing 1,3-dihydroxy-4,6-bis[α-methyl-α-(4'-hydroxyphenyl)ethyl]benzene which comprises the step of reacting resorcin with 4-isopropenylphenol in a single non-polar solvent or a single polar solvent in the presence of an acidic catalyst.

However, this method suffers from the following problems. Resorcin has a low solubility in a non-polar solvent and the majority of resorcin is dispersed in the solvent in its solid state. As a result, the reaction of resorcin with 4-isopropenylphenol is initiated in a heterogeneous reaction system and the solid resorcin remaining in the reaction system is dissolved in the system as the reaction proceeds. For this reason, the reaction is greatly influenced by the shapes and sizes of the solid resorcin particles dispersed in the reaction system. Moreover, control of the reaction is quite difficult since a part of the solid resorcin remaining in the reaction system is covered with the crystals of the intended product when it is crystallized in the system. On the other hand, if the reaction is performed in a polar solvent, these starting materials are reacted in a homogeneous solution system from the beginning to the end of the reaction. Therefore, the intended product, 1,3-dihydroxy-4,6-bis[α-methyl-α-(4'-hydroxyphenyl)ethyl]benzene, does not crystallize and therefore, the chemical equilibrium in the liquid phase does not cause a shift. This accordingly leads to a low reaction yield and reduction in the purity of the resulting product.

SUMMARY OF THE INVENTION

The object of the present invention is generally to solve the foregoing problems associated with the conventional technique and more specifically to provide a method for easily preparing highly pure 1,3-dihydroxy-4,6-bis[α-methyl-α-(4'-hydroxyphenyl)ethyl]benzene in a high yield.

The inventors of this invention have conducted various studies to accomplish the foregoing object, have found out that the foregoing problems can be solved by reacting resorcin with 4-isopropenylphenol in a mixed solvent comprising non-polar and polar solvents in the presence of an acidic catalyst and thus have completed the present invention.

One aspect of the present invention is a method for preparing 1,3-dihydroxy-4,6-bis[α-methyl-α-(4'-hydroxyphenyl)ethyl]benzene comprises the step of initiating the reaction of resorcin with 4-isopropenylphenol in a homogeneous system in a mixed solvent comprising a non-polar solvent and a polar solvent in the presence of an acidic catalyst.

Another aspect of the present invention is a method comprising the steps of dissolving 4-isopropenylphenol or a mixture of 4-isopropenylphenol with a linear polymer thereof in a mixed solvent comprising non-polar and polar solvents, then converting the 4-isopropenylphenol into an oligomer thereof in the presence of an acidic catalyst, adding resorcin to dissolve it in the oligomer solution and thereafter adding an acidic catalyst to cause a reaction of the resorcin with the resulting oligomer.

A still further aspect of the present invention is a method comprising the steps of dissolving 4-isopropenylphenol or a mixture of 4-isopropenylphenol with a linear polymer thereof, and resorcin in a mixed solvent comprising non-polar and polar solvents, then converting the 4-isopropenylphenol into an oligomer thereof in the presence of an acidic catalyst and thereafter adding an acidic catalyst to cause a reaction of the resorcin with the resulting oligomer.

1,3-Dihydroxy-4,6-bis[α-methyl-α-(4'-hydroxyphenyl) ethyl]benzene prepared by the methods of the present invention is represented by the following formula (1):

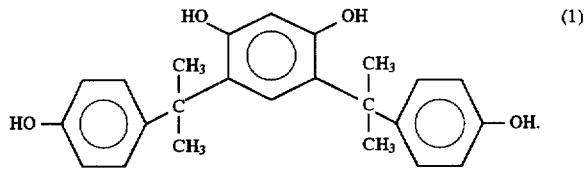

The method of the present invention is characterized by the use of a mixed solvent comprising non-polar and polar solvents and, in particular, the reaction is initiated in a homogeneous system in the method. This makes the control of the reaction quite easy. Moreover, the method ensures a quite high effect of recrystallization observed during separation of the desired product from the reaction system and this in turn results in the formation of the desired product having high purity.

DESCRIPTION OF THE PREFERRED EMBODIMENTS

The method of the present invention will hereunder be described in more detail.

Resorcin usable in the present invention may be those available on the market. As the 4-isopropenylphenol, there may be used, in the present invention, those obtained by cleaving, and for instance, dihydroxydiphenylpropane at 220° C. 50 mm Hg in the presence of sodium hydroxide to give a mixture of phenol, 4-isopropenylphenol and polymers of 4-isopropenylphenol (number of repeating units: 2 to 10) and then removing phenol from the mixture. In addition, it is also possible to use monomeric 4-isopropenylphenol isolated from the mixture, linear dimeric 4-methyl-2,4-bis (4-hydroxyphenyl)pentene-1 or 4-methyl-2,4-bis(4-hydroxyphenyl)pentene-2, or mixtures thereof. Moreover, the 4-isopropenylphenols usable herein may further include an oligomer obtained by oligomerizing 4-isopropenylphenol under the oligomerization conditions as will be detailed below. Further, the 4-isopropenylphenols usable herein may be those having properties identical to those of the foregoing 4-isopropenylphenols even if they are prepared by other methods.

The acidic catalysts usable in the present invention include, for instance, inorganic acids such as hydrobromic acid, hydrochloric acid and nitric acid. The amount of the acidic catalyst varies depending on the kinds of non-polar and polar solvents constituting the reaction solvent system used herein and mixing ratio of the former to the latter, but in general ranges from 0.0001 to 0.01% by weight for hydrobromic acid; 0.001 to 0.1% by weight for hydrochloric acid; and 0.01 to 1.0% by weight for nitric acid, on the basis of the weight of the reaction solution.

The amount of the 4-isopropenylphenol, the linear polymers of 4-isopropenylphenol (those having 2 to 10 repeating units and including the foregoing oligomers) or mixtures thereof relative to that of resorcin in general ranges from 1.8 to 2.5 moles and preferably 1.9 to 2.2 moles of the former (the molar number of the linear polymer of 4-isopropenylphenol is expressed in terms of the molar number of 4-isopropenylphenol units) per mole of resorcin. This is because if the former is used in an amount of less than 1.8 moles, the amount of 2-(2,4-dihydroxyphenyl)-2-(4-hydroxyphenyl)propane remaining in the reaction system increases, while if it exceeds 2.5 moles, the amount of 4-isopropenylphenol oligomers increases and this makes the purification step complicated.

The mixed solvent herein used as the reaction solvent comprises a mixture of a non-polar solvent and a polar solvent. Examples of non-polar solvents are aromatic hydrocarbons such as benzene, toluene and xylene; halogenated hydrocarbons such as dichloromethane and carbon tetrachloride; aliphatic hydrocarbons such as hexane; and alicyclic hydrocarbons such as cyclohexane. In addition, examples of polar solvents usable herein include alcohols such as methanol and ethanol. As such mixed solvents, there may be used those comprising one or two kinds of non-polar solvents and one or two kinds of polar solvents. Among these, mixed solvents preferably used comprise benzene and methanol.

Regarding the mixing ratio of the non-polar solvent to the polar solvent in the mixed solvent, the amount of the polar solvent is in general not more than 20% by weight and preferably 0.5 to 10% by weight based on the total weight of the mixed solvent.

The mixed solvent is used in such an amount that it can form a homogeneous reaction system at the beginning of the reaction and the amount thereof varies depending on the mixing ratio of the non-polar solvent to the polar solvent. The amount thereof is in general at least two times and preferably 3 to 10 times that of the total weight of resorcin and 4-isopropenylphenol, linear polymers of 4-isopropenylphenol or mixture thereof. If the amount is less than two times, the concentration of crystals in the reaction system is too high to agitate the reaction system.

The reaction temperature ranges from 0° to 100° C. and preferably 30° to 70° C. This is because if it is less than 0° C., the reaction requires a long time period, while if it exceeds 100° C., a large amount of impurities are formed.

The reaction time in general ranges from 0.5 to 20 hours and preferably 1 to 15 hours.

The reaction is generally carried out by charging, in a batch, 4-isopropenylphenols, resorcin and a mixed solvent in a reactor, dissolving the reactants in the solvent, then reacting them over a predetermined time while adding an acidic catalyst to the reaction system, followed by removing crystals from the reaction system to give a desired product. If 4-isopropenylphenol, or a mixture of 4-isopropenylphenol and a linear polymer thereof is used, however, the reactants undergo a vigorous exothermic reaction. For this reason, they are introduced into the reactor continuously or in portions, but this operation is quite complicated.

If 4-isopropenylphenol, or a mixture of 4-isopropenylphenol and a linear polymer thereof is introduced into the reactor in a batch, it is preferred to oligomerize 4-isopropenylphenol in advance and then react the resulting oligomer with resorcin. This is because the heat of reaction can easily be dissipated, any abrupt generation of heat can be prevented and thus the reaction temperature can easily be controlled.

The oligomerization of 4-isopropenylphenol can be carried out by dissolving, for instance, 4-isopropenylphenol, or a mixture of 4-isopropenylphenol and a linear polymer thereof in the foregoing mixed solvent used as the reaction solvent, maintaining the solution at 30° to 60° C., adding hydrobromic acid, hydrochloric acid or nitric acid in an amount generally ranging from 0.00005 to 0.0005% by weight, 0.0005 to 0.005% by weight or 0.005 to 0.05% by weight respectively and then maintaining the reaction mixture at that temperature for 10 to 30 minutes. After the oligomerization, resorcin is added to and dissolved in the mixture, then the foregoing acidic reaction catalyst is added thereto to thus react the resorcin with the resulting oligomer to give the desired product.

Alternatively, 4-isopropenylphenol, or a mixture of 4-isopropenylphenol and a linear polymer thereof, and resorcin are dissolved in the foregoing mixed solvent used as the reaction solvent, followed by oligomerization under conditions similar to the aforementioned oligomerization conditions, addition of the foregoing acidic reaction catalyst and reaction of the resorcin with the resulting oligomer. In this case, the 4-isopropenylphenols slightly undergo a reaction with resorcin during the oligomerization.

The acidic catalyst used in the oligomerization may be identical to or different from that used in the reaction. In general, it is preferred to use the same acidic catalyst in these processes from the viewpoint of the management of catalysts and the post-treatment of waste liquor.

After completion of the reaction, the reaction solution is filtered and the resulting crude crystals are washed with, for instance, benzene, toluene, cyclohexane and dichloromethane. Then the crystals are in general subjected to vacuum drying at a temperature ranging from 100° to 120° C. If the crystals are additionally washed with warm water after the washing with, for instance, benzene, the purity of the crystals can further be improved.

The present invention will be explained in more detail with reference to the following non-limitative working examples.

EXAMPLE 1

To a 1 l volume separable flask equipped with a reflux condenser, a thermometer and a stirring machine, there were added 80.4 g (0.6 mole) of 4-isopropenylphenol, 650 g of benzene and 14 g of methanol, followed by dissolution at 35° C., addition of 0.02 g of 36% by weight hydrochloric acid and stirring for 10 minutes to oligomerize 4-isopropenylphenol. Then 33 g (0.3 mole) of resorcin was added to and dissolved in the oligomer solution and then 0.3 g of 36% by weight hydrochloric acid was added to the solution to thus cause a reaction of resorcin with the oligomer at 45° C. for one hour with stirring. After completion of the reaction, the resulting slurry was subjected to suction filtration to separate crystals formed and the crystals were washed with 200 g of benzene. After air-drying, the crystals were dried at 120° C. for 3 hours in a vacuum dryer to give 97 g of the desired crystalline product having a melting point ranging from 217° to 219° C.

The crystals thus prepared were subjected to elemental analysis, mass spectrometric analysis and $^1$H-NMR spectroscopic analysis and the following results were obtained.

| Elemental Analysis: | C | H | N |
| --- | --- | --- | --- |
| Found | 76.0% | 6.9% | <0.05% |
| Calculated | 76.2% | 6.9% | — |

Mass Spectrometric Analysis (EI-MS): $M^+$=378

$^1$H-NMR spectroscopic analysis [in $CD_3COCD_3$; Reference Material: tetramethylsilane (TMS)]

| δ (ppm) | Attribution * |
| --- | --- |
| 1.68 (s, 12H) | (a) |
| 6.18 (s, 1H) | (b) |
| 6.53–7.24 (q, 8H) | (c), (d) |
| 6.90 (s, 2H) | (e) |
| 7.33 (s, 1H) | (f) |
| 8.02 (s, 2H) | (g) |

Note: * Each symbol represents the position of a specific carbon atom in the compound represented by the following structural formula (1).

The results of the foregoing analyses clearly indicate that the product prepared in Example 1 is 1,3-dihydroxy-4,6-bis [α-methyl-α-(4'-hydroxyphenyl)ethyl]benzene represented by the following formula (1):

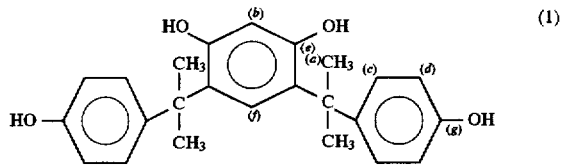

and the product has a purity of 99.5% by weight as determined by liquid chromatography. The conditions for the reaction and the results obtained are summarized in Table 1 given later.

EXAMPLE 2

To the same container used in Example 1, there were added 80.4 g (0.6 mole as expressed in terms of the molar number of 4-isopropenylphenol unit) of a linear dimer of 4-isopropenylphenol, 33 g (0.3 mole) of resorcin, 600 g of benzene and 16 g of methanol, followed by dissolution while stirring the mixture at 45° C. for one hour. Then the reaction was carried out at 45° C. for one hour with stirring, while adding 0.3 g of 36% by weight hydrochloric acid. After completion of the reaction, the reaction system was neutralized by addition of 1.3 ml of a 2N methanol solution of KOH. The resulting slurry was subjected to suction filtration to separate crystals formed and the crystals were washed with 200 g of benzene. The resulting wet crystals and 800 g of water were introduced into a flask, then the benzene was distilled off by increasing the temperature to 80° C., followed by suction filtration at 50° C. and washing with 200 g of warm water maintained at 50° C. The resulting crystals were dried at 120° C. for 3 hours in a vacuum dryer to give 90 g of the desired crystalline product. The product has a purity of 99.8% by weight as determined by liquid chromatography. The conditions for the reaction and the results obtained are summarized in Table 1 given later.

EXAMPLE 3

To the same container used in Example 1, there were added 107.2 g (0.8 mole) of 4-isopropenylphenol, 44 g (0.4 mole) of resorcin, 650 g of benzene and 15 g of methanol, followed by dissolution at 50° C. and oligomerization of 4-isopropenylphenol for 20 minutes with stirring while adding 0.02 g of 20% by weight hydrochloric acid. Then the reaction was carried out at 60° C. for 2 hours with stirring while adding 0.25 g of 20% by weight hydrochloric acid and then cooling the reaction system to 50° C. for an additional one hour with stirring. The resulting slurry was subjected to suction filtration to separate crystals formed and the crystals were washed with 300 g of benzene. The resulting crystals were air-dried and then dried at 120° C. for 3 hours in a vacuum dryer to give 130 g of the desired product as crystals. The product has a purity of 99.4% by weight as determined by liquid chromatography. The conditions for the reaction and the results obtained are summarized in Table 1 given below.

EXAMPLES 4 AND 5

The same procedures used in Example 3 were repeated except for the conditions shown in Table 1 to prepare 1,3-dihydroxy-4,6-bis|α-methyl-α-(4'-hydroxyphenyl) ethyl]benzene. The conditions for the reaction and the results obtained are summarized in Table 1 given below.

COMPARATIVE EXAMPLE 1

To the same container used in Example 1, there were added 80.4 g (0.6 mole) of 4-isopropenylphenol and 650 g of benzene, followed by dissolution at 35° C. and oligomerization of 4-isopropenylphenol for 10 minutes with stirring while adding 0.02 g of 36% by weight hydrochloric acid. Then 33 g (0.3 mole) of resorcin was added to the oligomer solution and the reaction was carried out at 45° C. for one hour with stirring while adding 0.3 g of 36% by weight hydrochloric acid. After completion of the reaction, the resulting slurry was subjected to suction filtration to separate crystals formed and the crystals were washed with 200 g of benzene. The resulting crystals were air-dried and then dried at 120° C. for 3 hours in a vacuum dryer to give 102 g of the desired crystalline product. The product has a purity of 97.7% by weight as determined by liquid chromatography. The conditions for the reaction and the results obtained are summarized in Table 1 given below.

COMPARATIVE EXAMPLE 2

To the same container used in Example 1, there were added 80.4 g (0.6 mole) of 4-isopropenylphenol, 33 g (0.3 mole) of resorcin and 400 g of methanol, followed by dissolution at 45° C. and reaction at 45° C. for one hour with stirring while adding 5 g of 36% by weight hydrochloric acid. After completion of the reaction, 250 g of water was added to the reaction system, owed by cooling down to 10° C. to crystallize, suction filtration to separate crystals formed and washing them with 200 g of water. The resulting crystals were dried at 120° C. for 3 hours in a vacuum dryer to give 63 g of the desired crystalline product. The product has a purity of 89.5% by weight as determined by liquid chromatography. The conditions for the solution and the results obtained are summarized in Table 1 given below.

TABLE 1

| Ex. No. | Kind of Catalyst Used Amount in Olig. S.[1] | Kind of Catalyst Used Amount in Reac. S.[2] | Solv. Mixing Ratio[3] | Concn. of MeOH[4] | Reac. Temp. × Reac. Time | Purity (%) | Yield (%)[5] |
|---|---|---|---|---|---|---|---|
| 1 | 36% by weight HCl 0.02 g | 0.3 g | 5.86 | 2.1 | 45° C. × 1 hr. | 99.5 | 85.5 |
| 2 | 36% by weight HCl — | 0.3 g | 5.43 | 2.6 | 45° C. × 1 hr. | 99.8 | 83.8 |
| 3 | 20% by weight HCl 0.02 g | 0.25 g | 4.40 | 2.3 | 60° C. × 2 hr. + 50° C. × 1 hr. | 99.4 | 86.0 |
| 4 | 5% by weight HBr 0.02 g | 0.25 g | 4.40 | 2.3 | 60° C. × 2 hr. + 50° C. × 1 hr. | 99.5 | 87.0 |
| 5 | 61% by weight HNO$_3$ 0.25 g | 2.5 g | 4.40 | 2.3 | 60° C. × 4 hr. + 50° C. × 2 hr. | 99.2 | 80.0 |
| 1* | 36% by weight HCl 0.02 g | 0.3 g | 5.73 | — | 45° C. × 1 hr. | 97.7 | 89.9 |
| 2* | 36% by weight HCl — | 5.0 g | 3.53 | 100 | 45° C. × 1 hr. | 89.5 | 55.6 |

Note:
[1] This means the amount of the catalyst used in the oligomerizaion step (Olig. S.).
[2] This means the amount of the catalyst used in the reaction step (Reac. S.).
[3] Weight ratio: solvent/(4-isopropenylphenol + resorcin).
[4] The amount of methanol in solvent (% by weight).
[5] The amount (mole) of the product per mole of the charged resorcin (mole %).
*: Comparative Example.

As seen from the results obtained in Examples, the method of the present invention can easily be handled, ensures a high yield, permits the reduction of impurity content (for instance, the impurity concentration in the product obtained in Example 1 is 0.5%, while that in the product obtained in Comparative Example 1 is 2.3%, i.e., it is reduced by a factor of 1/5) and can provide highly pure 1,3-dihydroxy-4,6-bis[α-methyl-α-(4'-hydroxyphenyl) ethyl]benzene. The resulting phenolic compound is useful as, for instance, a branching agent for polycarbonates, polyesters or the like; a raw material for radiant ray-sensitive components for use as resist materials; a raw material for epoxy resins; and a hardening agent for epoxy resins.

What is claimed is:

1. A method for preparing 1,3-dihydroxy-4,6-bis[α-methyl-α(4'-hydroxyphenyl)ethyl]benzene comprising the step of initiating a homogeneous reaction of resorcin with 4-isopropenylphenol in a mixed solvent of a non-polar solvent selected from the group consisting of benzene, toluene and xylene and a polar solvent selected from the group consisting of methanol and ethanol in the presence of an inorganic acid selected from the group consisting of hydrochloric acid, hydrobromic acid and nitric acid.

2. The method as set forth in claim 1 wherein the non-polar solvent is benzene and the polar solvent is methanol.

3. The method as set forth in claim 1 wherein the 4-isopropenylphenol is at least one phenolic compound selected from the group consisting of 4-isopropenylphenol and linear polymers of 4-isopropenylphenol.

4. The method as set forth in claim 1 wherein the non-polar solvent is benzene, the polar solvent is methanol and the 4-isopropenylphenol is at least one phenolic compound selected from the group consisting of 4-isopropenylphenol and linear polymers of 4-isopropenylphenol.

5. The method as set forth in claim 1 wherein the method further comprises dissolving 4-isopropenylphenol, or a mixture of 4-isopropenylphenol and a linear polymer of 4-isopropenylphenol in said mixed solvent, oligomerizing the 4-isopropenylphenol in the presence of an acidic catalyst, then adding resorcin to the oligomerization reaction system to dissolve the resorcin, adding and acidic catalyst to the reaction system and reacting resorcin with the resulting oligomer.

6. The method as set forth in claim 5 wherein the non-polar solvent is benzene and the polar solvent is methanol.

7. The method as set forth in claim 1 wherein the method further comprises dissolving 4-isopropenylphenol, or a mixture of 4-isopropenylphenol and a linear polymer of 4-isopropenylphenol, and resorcin in said mixed solvent, oligomerizing the 4-isopropenylphenol in the presence of an acidic catalyst, adding an acidic catalyst to the reaction system and then reacting resorcin with the resulting oligomer.

8. The method as set forth in claim 7 wherein the non-polar solvent is benzene and the polar solvent is methanol.